United States Patent [19]
Ramirez et al.

[11] Patent Number: 5,409,706
[45] Date of Patent: * Apr. 25, 1995

[54] ANHYDROUS FOAMING COMPOSITION CONTAINING LOW CONCENTRATIONS OF DETERGENTS AND HIGH LEVELS OF GLYCERIN AND EMOLLIENTS SUCH AS OILS AND ESTERS

[75] Inventors: Jose E. Ramirez, Trumbull; Mohan Vishnupad, Monroe, both of Conn.

[73] Assignee: Imaginative Research Associates, Inc., Bridgeport, Conn.

[*] Notice: The portion of the term of this patent subsequent to Oct. 19, 2010 has been disclaimed.

[21] Appl. No.: 42,617

[22] Filed: Apr. 2, 1993

Related U.S. Application Data

[63] Continuation-in-part of Ser. No. 878,363, May 4, 1992, Pat. No. 5,254,334.

[51] Int. Cl.$^6$ .......................... A61K 7/00; A61K 7/06
[52] U.S. Cl. .................... 424/401; 424/70.1; 514/846; 252/162; 252/DIG. 5
[58] Field of Search ............ 424/70, 78.03, 401; 514/846; 252/162, DIG. 5

[56] References Cited

U.S. PATENT DOCUMENTS

| | | | |
|---|---|---|---|
| 3,224,976 | 12/1965 | Farrar et al. | 252/119 |
| 3,829,563 | 8/1974 | Barry et al. | 424/70 |
| 4,405,492 | 9/1983 | Nyquist | 252/370 |
| 4,707,293 | 11/1987 | Ferro | 252/174.17 |
| 4,808,322 | 2/1989 | McLaughlin | 252/121 |
| 4,812,253 | 3/1989 | Small | 252/132 |
| 4,829,092 | 8/1989 | Nelson et al. | 514/738 |
| 4,851,147 | 7/1989 | Esposito | 252/108 |
| 4,931,204 | 6/1990 | Ramirez et al. | 252/167 |
| 5,002,680 | 3/1991 | Schmidt | 252/90 |
| 5,254,334 | 10/1993 | Ramirez | 424/70 |

FOREIGN PATENT DOCUMENTS

| | | |
|---|---|---|
| 1290689 | 10/1991 | Canada. |
| 460839 | 2/1937 | United Kingdom. |

OTHER PUBLICATIONS

Chem. Abstract, 5913f (1964), Toilet bar soap.
Chem. Abstracts, 95:45134z, Mar-resistant soap bar.
Chem. Abstracts, 20850f, Detergent and spot-removing composition.
Chem. Abstracts, 5747h, Metallic soap-petrolatum ointment bases.
Chem. Abstract, Brit., 29, 113; Dec. 13, 1909.
Chem. Abstracts, 98160V (1969), Superfatted soaps.
Catalog; Macalaster Bicknell Co., New Haven, Conn. (1988).
Seidenfaden, M. L., The use of taurides, sarcosides and isethionates in cosmetics, American Perfumer and Cosmetics vol. 81; pp. 29–32, Aug. 1966.

*Primary Examiner*—Thurman K. Page
*Assistant Examiner*—Sally Gardner
*Attorney, Agent, or Firm*—Dilworth & Barrese

[57] ABSTRACT

Cosmetically elegant anhydrous foaming creams contain high levels of glycerin and emollients, sodium cocoyl isethionate at levels of 19% or less and an effective amount of a detergent additive to increase the softness of the composition. The detergent additive is preferably one of the following: sodium lauryl sulfate, a sodium salt of fatty acid taurate, an acyl glutamate, an $\alpha$-olefin sulfonate or a neutralized lauryl phosphoric acid. The detergent additive can be present in an amount from about 1 to about 20 weight percent.

16 Claims, No Drawings

ANHYDROUS FOAMING COMPOSITION CONTAINING LOW CONCENTRATIONS OF DETERGENTS AND HIGH LEVELS OF GLYCERIN AND EMOLLIENTS SUCH AS OILS AND ESTERS

RELATED APPLICATIONS

This application is a continuation-in-part of U.S. application Ser. No. 07/878,363, now U.S. Pat No. 5,254,334.

FIELD OF THE INVENTION

This invention relates generally to formulations of anhydrous, foaming, cosmetically elegant creams having a high glycerin and emollient content and containing sodium cocoyl isethionate in combination with a detergent additive to give the creams a desirable consistency.

More particularly, this invention is concerned with the discovery that low levels of sodium cocoyl isethionate and certain detergent additives in combination with high concentrations of glycerin and high levels of emollients (petrolatum, 1-Decene polymer (hydrogenated), mineral oils and esters) can be formulated into anhydrous, cosmetically elegant foaming cream.

A unique feature of such composition is that the low levels of detergent and high level of glycerin and emollients provide the maximum functional benefits to skin by providing good foam without any defatting of the skin.

A novel finding of these compositions is the effect of detergents selected from the group consisting of sodium salts of fatty acid taurate, acyl glutamates, sodium lauryl sulfate, alpha-olefin sulfonate and lauryl phosphoric acid neutralized in producing the soft, easily processible cream. These detergents in the presence of sodium cocoyl isethionate, glycerin and emollients tends to soften the cream significantly, with the softening effect being observed at contents of about one to about 20 percent by weight depending on the particular detergent employed.

Another unique finding is the compatibility of acyl glutamate by itself in the high glycerin containing compositions, without the presence of sodium cocoyl isethionate. It has unexpectedly been found that functional, cosmetically elegant anhydrous creams can be formulated using acyl glutamate, emollients and glycerin.

BACKGROUND OF THE INVENTION

Prior to the present invention, it was known from Canadian Patent Number 1,290,689 entitled High Oil Containing Anhydrous Foamable Composition, that high levels of petrolatum in combination with high levels of detergents, such as sodium cocoyl isethionate, overcomes the foam suppressing properties of the oil so as to provide an extremely functional, stable, good foaming in cosmetically attractive products.

The prior anhydrous foam oil systems require a high level of petrolatum and mineral oil in the range of 30 to 50 percent by weight, detergent sodium cocoyl isethionate in the level of 20 to 80 percent by weight and additives, such as glycerin, in the level of 0 to 10 percent by weight.

The present invention differs from the above composition in that we find high levels of glycerin in the range of 30-60 percent with oils and esters of petrolatum consistency in the range of 10 to 40 percent, sodium cocoyl isethionate at 10 to 19 percent and certain detergent additives in the range of 1 to 20 percent, depending on the detergent selected, provide an extremely functional, good consistency, foaming cleanser which is cosmetically elegant.

One important discovery in our compositions is the effect of certain detergent additives on the consistency of the anhydrous foaming cream. For example, sodium lauryl sulfate or sodium salts of fatty acid taurate at a level of 1 to 5 percent softens the cream consistency significantly with an optimum softening effect with sodium lauryl sulfate being seen at the 3 percent level. As other examples, acyl glutamate in the range of 1–19 percent or alpha olefin sulfonate in the range of 1–15 percent produce similar softening effects in the high glycerin compositions. This softening effect of these detergents in the high level of glycerin, oils and esters of petrolatum consistency with low level of sodium cocoyl isethionate, permits the production of the cosmetically acceptable, soft creams. The processing of such soft creams is much easier during the manufacturing of such products.

SUMMARY OF THE INVENTION

The present invention combines sodium cocoyl isethionate at levels of 19 percent or less with high concentrations of glycerin and emollients, such as oils and esters of petrolatum consistency and an effective amount of a detergent additive for increasing the softness of the composition so as to form highly useful anhydrous composition capable of foaming when combined with water during use.

Preferably the anhydrous cream composition of the present invention comprise:
  a) glycerin in the amount from about 30 to about 60 percent by weight based on the total weight of the composition;
  b) emollients in an amount from about 10 to about 40 percent by weight based on the weight of the total composition;
  c) sodium cocoyl isethionate in an amount from about 10 to about 19 percent by weight based on the weight of the total composition; and
  d) an effective amount of a detergent additive for increasing the softness of the composition. In particularly useful compositions, the detergent additive is selected from the group consisting of sodium lauryl sulfate, sodium salts of fatty acid taurate, acyl glutamates, α-olefin sulfonate and neutralized lauryl phosphoric acid. The effective amount depends upon the particular detergent additive employed, but will normally range from between one and 20 percent by weight based on the total weight of the composition.

In cases where oils and esters are employed as emollients in the compositions, small amounts of microcrystalline waxes may also be added.

In addition, the anhydrous foaming creams of the present invention may have incorporated therein one or more active ingredients for delivery to the skin during use.

In another aspect, compositions of this invention are soft, foaming creams containing acyl glutamate in an amount from about one to about 20 percent, glycerin in an amount from about 30 to about 60 percent, and oils and esters of petrolalum consistency in an amount from about 10 to about 40 percent.

DETAILED DESCRIPTION OF THE INVENTION

The compositions of the present invention preferably contain glycerin in an amount of from about 30 to about 60 percent by weight; sodium cocoyl isethionate in an amount of less than 19 percent by weight; emollients in an amount from about 10 to about 40 percent by weight; and a detergent additive in an amount effective for increasing the softness of the composition. In particularly useful embodiments, the detergent additive is selected from the group of detergents consisting of sodium lauryl sulfate, sodium salts of fatty acid taurate, acyl glutamates, α-olefin sulfonates and neutralized lauryl phosphoric acid. The amount of the softening detergent additive included in the composition should be an amount effective to increase the softness of the composition. Preferably, the ratio of detergent additive to sodium cocoyl isethionate is in the range of about 1:6 to about 1:1. While the precise amount of softening detergent employed will depend upon the particular detergent employed, normally the softening detergent additive will be present in an amount from about one to about 20 weight percent. For example, when sodium lauryl sulfate is used as the softening detergent additive, an effective amount will be between about 1 to about 5 percent by weight. Preferably, the ratio of sodium lauryl sulfate to sodium cocoyl isethionate in the composition is in the range of about 1:3 to about 1:6.

Effective amounts of other detergent additives are as follows:

| Detergent Additive | Effective Amount |
| --- | --- |
| Sodium salts of fatty acid taurate | 1–5 weight percent |
| Acyl glutamates | 1–19 weight percent |
| α-olefin sulfonates | 1–15 weight percent |
| neutralized lauryl phosphoric acids | 3–7 weight percent |

Emollients suitable for use in the compositions of the present invention include petrolatum, mineral oils, and esters such as, for example, isopropyl myristate, isopropyl palmitate, 1-Decene polymer (hydrogenated) and $C_{12}$–$C_{15}$ alcohol benzoates. In the case of oils and esters, a small amount of microcrystalline wax may be added to produce a cosmetically acceptable cream. Typically, microcrystalline wax will be present in an amount from about 4 to about 10 percent by weight.

In addition to the foregoing components, foam boosters may be incorporated into the compositions of the present invention. Suitable foam enhancers include potassium polymetaphosphate, n-pentane, isopentane, sodium lauryl sulfoacetate, sodium lauryl sulfate, amides and sarcosynates. These materials will enhance the foam produced when the present anhydrous cream compositions are exposed to water during use.

The compositions of this invention may also contain additives such as fragrance, color, sugar, sugar derivatives and gums, such as, for example xanthan gum, to improve the texture, appearance and user perception of the cream. Additionally, active ingredients may be incorporated in the present compositions. Such active ingredients include, but are not limited to deodorants, medicaments such as, for example coal-tar, benzoyl peroxide, vitamin A and vitamin E, and antibacterial ingredients such as, for example, triclosan, PVP-iodine and salicylic acid.

While the cream compositions of this invention are described as anhydrous, it should be understood that a certain amount of water of hydration associated with the various components may be contained in the composition. Typically, this water of hydration will be less than five percent by weight.

The compositions of the present invention may be prepared by vigorously mixing the ingredients together. The order or addition is not critical. Preferably, and in the Examples which follow, the compositions were prepared as follows: Sodium cocoyl isethionate is added to glycerin heated to 80° C. The mixture is homogenized once the detergent flakes have melted into the glycerin. The softening detergent additive is then added, with continued homogenizing, to the detergent/glycerin phase followed by addition of the oil phase which has been heated to 80° C. Fragrance is added to the composition after the homogenous white cream has cooled somewhat.

The consistency of the cream produced was tested after overnight storage of the cream at ambient temperature using a Penetrometer (Penetrometer, Universal, ASTM, (Precision 73510), Catalog No. 33541, Macalaster Bicknell Company of Connecticut, Inc., New Haven, Conn.) which was equipped with a 25 gram cone. The amount of penetration of the cone into the sample was displayed by, and read off of the pentrometer in units of mm×10. A lower penetration value indicates a harder cream. Preferably, the creams of this invention have a penetration value greater than about 130 mm×10.

EXAMPLES 1 TO 10

The compositions of Examples 1 to 10 show the effect that changing the amount of sodium lauryl sulfate in the composition has on the consistency of the anhydrous cream.

In examples 1 to 4, the formulations of which are presented in Table I, the emollient employed is petrolatum. Comparative Example A contains no sodium lauryl sulfate. As can be seen from Examples 1 to 4, the addition of sodium lauryl sulfate of up to 5% improved the consistency of the cream compared to the cream composition containing no sodium lauryl sulfate (Comparative Example A) and the cream composition containing 10% sodium lauryl sulfate. The softest cream produced, having a penetration value of 185, was produced by a sodium lauryl sulfate content of 3% by weight, with the cream being somewhat harder at sodium lauryl sulfate contents below (1%) and above (5%).

TABLE I

| Example No. | A | 1 | 2 | 3 | 4 |
| --- | --- | --- | --- | --- | --- |
| Sodium Cocoyl Isethionate | 20 | 19 | 17 | 15 | 10 |
| Sodium Lauryl Sulfate | 0 | 1 | 3 | 5 | 10 |
| Glycerin | 50 | 50 | 50 | 50 | 50 |
| Petrolatum | 30 | 30 | 30 | 30 | 30 |
| Penetration Value (mm × 10) | 80 | 125 | 185 | 130 | 80 |

In Examples 5 to 7, the formulations of which are in Table II, the emollient employed is mineral oil, and microcrystalline wax (6%) has been added. As in evident from Table II, a 3% sodium lauryl sulfate content again produced the softest cream (penetration value 160) compared to slightly lower and slightly higher sodium lauryl sulfate contents.

TABLE II

| Example No. | B | 5 | 6 | 7 |
|---|---|---|---|---|
| Sodium cocoyl isethionate | 20 | 19 | 17 | 15 |
| Sodium lauryl sulfate | 0 | 1 | 3 | 5 |
| Mineral oil | 24 | 24 | 24 | 24 |
| Microcrystalline wax | 6 | 6 | 6 | 6 |
| Glycerin | 50 | 50 | 50 | 50 |
| Penetration Value (mm × 10) | 145 | 105 | 160 | 120 |

Examples 8 to 10 further demonstrate that a sodium lauryl sulfate content of 3% provides the softest cream, compared to lower and higher sodium lauryl sulfate levels. In Examples 8 to 10, the emollient employed is an ester; namely isopropyl palmitate. The formulations and penetration values for Example 8 to 10 as well as Comparative Example C (containing no sodium lauryl sulfate) are presented in Table III.

TABLE III

| Example No. | C | 8 | 9 | 10 |
|---|---|---|---|---|
| Sodium cocoyl isethionate | 20 | 19 | 17 | 15 |
| Sodium lauryl sulfate | 0 | 1 | 3 | 5 |
| Isopropyl palmitate | 24 | 24 | 24 | 24 |
| Microcrystalline wax | 6 | 6 | 6 | 6 |
| Glycerin | 50 | 50 | 50 | 50 |
| Penetration value (mm × 10) | 180 | 175 | 180 | 100 |

Examples 11 and 12 further demonstrate that a sodium lauryl sulfate content of 3% provides the softest cream, compared to lower and higher sodium lauryl sulfate levels. In Examples 11 and 12, the emollient employed is 1-decene polymer (hydrogenated). The formulations and penetration values for Examples 11 and 12 as well as Comparative Example D (containing no sodium lauryl sulfate) are presented in Table IV.

TABLE IV

| Example No. | D | 11 | 12 |
|---|---|---|---|
| Sodium cocoyl isethionate | 20 | 17 | 15 |
| Sodium lauryl sulfate | 0 | 3 | 5 |
| 1-Decene, polymer hydrogenated | 24 | 24 | 24 |
| Microcrystalline Wax | 6 | 6 | 6 |
| Glycerin | 50 | 50 | 50 |
| Penetration Value (mm × 10) | 160 | 400+ | 150 |

EXAMPLE 13 TO 29

The compositions of Examples 13 to 29 show the effect that changing the amount of three detergent additives in the composition has on the consistency of the anhydrous cream.

| Example | E | 13 | 14 | 15 | 16 | 17 |
|---|---|---|---|---|---|---|
| Sodium Cocoyl Isethionate | 20 | 19 | 17 | 15 | 12 | — |
| Acyl glutamate | — | 1 | 3 | 5 | 8 | 20 |
| Petrolatum | 30.0 | 30 | 30 | 30 | 30 | 30 |
| Glycerin | 50 | 50 | 50 | 50 | 50 | 50 |
| Penetration Value (mm × 10) | 80 | 170 | +400 | +270 | +400 | 250 |

| Example | F | 18 | 19 | 20 | 21 | 22 |
|---|---|---|---|---|---|---|
| Sodium Cocoyl Isethionate | 20 | 19 | 17 | 15 | 12 | — |
| Alfa olefin sulfonate | — | 1 | 3 | 5 | 8 | 20 |
| Petrolatum | 30 | 30 | 30 | 30 | 30 | 30 |
| Glycerin | 50 | 50 | 50 | 50 | 50 | 50 |
| Penetration Value | 80 | 210 | 350 | 290 | 260 | 80 |

| Example | G | 23 | 24 | 25 | 26 |
|---|---|---|---|---|---|
| Sodium Cocoyl Isethionate | 20 | 19 | 17 | 15 | 12 |
| Sodium Methyl Cocoyl Taurate | — | 1 | 3 | 5 | 8 |
| Petrolatum | 30 | 30 | 30 | 30 | 30 |
| Glycerin | 50 | 50 | 50 | 50 | 50 |
| Penetration Value | 80 | 190 | +400 | 125 | 85 |

| | 27 | 28 | 29 |
|---|---|---|---|
| Lauryl Phosphoric Acid | 1 | 5 | 10 |
| TEA | 0.5 | 2.5 | 5 |
| Sodium Cocoyl Isethionate | 19 | 15 | 10 |
| Glycerin | 49.54 | 47 | 44 |
| Petroleum Jelly | 30 | 30 | 30 |
| Penetration Value | 90 | 130 | 75 |

EXAMPLES 30 TO 53

The following are specific, non-limiting, examples of compositions in accordance with the present invention.

EXAMPLE 30

| Ingredient | % |
|---|---|
| Sodium Cocoyl Isethionate | 12.00 |
| Sodium Lauryl Sulfate | 3.00 |
| Petrolatum (USP) | 30.00 |
| Glycerin (USP) | 55.00 |

| Ingredient | % |
|---|---|
| Sodium Cocoyl Isethionate | 12.00 |
| Sodium Lauryl Sulfate | 3.00 |
| Petrolatum (USP) | 25.00 |
| Glycerin | 59.95 |
| Xanthan Gum | 0.05 |

| Ingredient | % |
|---|---|
| Sodium Cocoyl Isethionate | 12.00 |
| Sodium Lauryl Sulfate | 2.00 |
| Sodium Lauryl Sulfoacetate | 1.00 |
| Petrolatum (USP) | 30.00 |
| Glycerin | 55.00 |

EXAMPLE 33

| Ingredient | % |
|---|---|
| Sodium Cocoyl Isethionate | 12.00 |
| Sodium Lauryl Sulfate | 3.00 |
| Petrolatum (USP) | 30.00 |
| Potassium Polymetaphosphate | 0.50 |
| Glycerin | 54.00 |
| Perfume | 0.50 |

EXAMPLE 34

| Ingredient | % |
|---|---|
| Sodium Cocoyl Isethionate | 16.00 |
| Sodium Lauryl Sulfate | 3.00 |
| Petrolatum (USP) | 27.00 |
| Glycerin | 54.00 |

EXAMPLE 35

| Ingredient | % |
| --- | --- |
| Sodium Cocoyl Isethionate | 12.00 |
| Sodium Lauryl Sulfate | 3.00 |
| Petrolatum | 27.00 |
| $C_{12-15}$ Alcohol Benzoate | 3.00 |
| Glycerin | 55.00 |

EXAMPLE 36

| Ingredient | % |
| --- | --- |
| Sodium Cocoyl Isethionate | 12.00 |
| Sodium Lauryl Sulfate | 3.00 |
| Petrolatum | 25.00 |
| Mineral Oil | 5.00 |
| N - Pentane | 5.00 |
| Glycerin | 50.00 |

EXAMPLE 37

| Ingredient | % |
| --- | --- |
| Sodium Cocoyl Isethionate | 12.00 |
| Sodium Lauryl Sulfate | 3.00 |
| Mineral Oil | 20.00 |
| Micro Crystalline Wax | 10.00 |
| Glycerin | 55.00 |

EXAMPLE 38

| Ingredient | % |
| --- | --- |
| Sodium Cocoyl Isethionate | 12.00 |
| Sodium Lauryl Sulfate | 3.00 |
| Isopropyl Palmitate | 24.00 |
| Micro Crystalline Wax | 6.00 |
| Glycerin | 55.00 |

EXAMPLE 39

| Ingredient | % |
| --- | --- |
| Sodium Cocoyl Isethionate | 12.00 |
| Sodium Lauryl Sulfate | 3.00 |
| Petrolatum (USP) | 30.00 |
| Dimethicone | 2.00 |
| Mineral Oil | 2.00 |
| Perfume | 0.30 |
| Glycerin | 50.70 |

EXAMPLE 40

| Ingredient | % |
| --- | --- |
| Sodium Cocoyl Isethionate | 10.00 |
| Sodium Lauryl Sulfoacetate | 2.00 |
| Sodium Lauryl Sulfate | 3.00 |
| Petrolatum (USP) | 30.00 |
| Mineral Oil | 3.00 |
| Perfume | 0.30 |
| Glycerin | 51.70 |

EXAMPLE 41

| Ingredient | % |
| --- | --- |
| Sodium Cocoyl Isethionate | 12.00 |
| Acyl Glutamate | 3.00 |
| Petrolatum (USP) | 33.00 |
| Potassium Poly Phosphate | 0.50 |
| Glycerin | 51.50 |

EXAMPLE 42

| Ingredient | % |
| --- | --- |
| Sodium Cocoyl Isethionate | 12.00 |
| Acyl Glutamate | 3.00 |
| Petrolatum (USP) | 33.00 |
| Parachlorometaxylenol | 0.5 |
| Potassium Polyphosphate | 0.5 |
| Glycerin | 51.5 |

EXAMPLE 43

| Ingredient | % |
| --- | --- |
| Sodium Cocoyl Isethionate | 12.00 |
| Alfa Olefin Sulfonate | 3.00 |
| Petrolatum (USP) | 30.00 |
| Potassium Polyphosphate | 0.5 |
| Glycerin | 51.5 |
| Mineral Oil | 3.0 |

EXAMPLE 44

| Ingredient | % |
| --- | --- |
| Sodium Cocoyl Isethionate | 12 |
| Alfa Olefin Sulfonate | 3 |
| Isopropyl Palmitate | 20 |
| Microcrystalline Wax | 10 |
| Glycerin | 55 |

EXAMPLE 45

| Ingredient | % |
| --- | --- |
| Sodium Cocoyl Isethionate | 12 |
| Acyl Glutamate | 3 |
| Isopropyl Palmitate | 20 |
| Microcrystalline Wax | 10 |
| Glycerin | 55 |

| Ingredient | % |
| --- | --- |
| Sodium Cocoyl Isethionate | 12 |
| Sodium Methyl Cocoyl Taurate | 3 |
| Mineral Oil | 20 |
| Microcrystalline Wax | 10 |
| Glycerin | 55 |

| Ingredient | % |
| --- | --- |
| Sodium Cocoyl Isethionate | 12 |
| Alfa Olefin Sulfonate | 3 |
| Mineral Oil | 20 |
| Microcrystalline Wax | 10 |

-continued

| Ingredient | % |
| --- | --- |
| Glycerin | 55 |

EXAMPLE 48

| Ingredient | % |
| --- | --- |
| Sodium Cocoyl Isethionate | 12 |
| Acyl Glutamate | 3 |
| Mineral Oil | 20 |
| Microcrystalline Wax | 10 |
| Glycerin | 55 |

EXAMPLE 49

| Ingredient | % |
| --- | --- |
| Sodium Cocoyl Isethionate | 12 |
| Sodium Methyl Cocoyl Taurate | 3 |
| Mineral Oil | 20 |
| Microcrystalline Wax | 10 |
| Glycerin | 55 |

EXAMPLE 50

| Ingredient | % |
| --- | --- |
| Sodium Cocoyl Isethionate | 12 |
| Sodium Methyl Cocoyl Taurate | 3 |
| Petrolatum USP | 30 |
| Potassium Polyphosphate | 0.5 |
| Mineral Oil | 3.0 |
| Glycerin | 51.5 |

EXAMPLE 51

| Ingredient | % |
| --- | --- |
| Sodium Cocoyl Isethionate | 12 |
| Lauryl Phosphoric Acid | 5 |
| Triethanolamine | 2.5 |
| Petrolatum | 30.0 |
| Glycerin | 50.5 |

EXAMPLE 52

| Ingredient | % |
| --- | --- |
| Sodium Cocoyl Isethionate | 12 |
| Alfa Olefin Sulfonate | 5 |
| Petrolatum | 33 |
| Potassium Polyphosphate | 0.5 |
| Sugar | 19.0 |
| Titanium Dioxide | 0.5 |
| Glycerin | 30.0 |

EXAMPLE 53

| Ingredient | % |
| --- | --- |
| Sodium Cocoyl Isethionate | 12 |
| Alfa Olefin Sulfonate | 5 |
| Petrolatum | 33 |
| Potassium Polyphosphate | 0.5 |
| Sugar | 3.0 |
| 1-Decene polymer, hydrogenated | 3.0 |
| Glycerin | 43.0 |

-continued

| Ingredient | % |
| --- | --- |
| Perfume | 0.5 |

It is to be understood that the above described embodiments of the invention wherein the cream softening effect of the composition of high concentration of glycerin, sodium cocoyl isethionate or acyl glutamate and emollients are achieved by certain specific detergent additives are illustrative only and that modifications to the above mentioned compositions may occur to those skilled in the art. Accordingly, this invention is not to be regarded as limited to the embodiment disclosed herein but is to be limited as defined by the appended claims.

We claim:

1. A composition comprising an anhydrous cream containing:
   a) glycerin in an amount from about 30 to about 60% by weight based on the weight of the total composition;
   b) sodium cocoyl isethionate in an amount up to about 19% by weight based on the weight of the total composition;
   c) emollients in an amount from about 10 to about 40% by weight based on the weight of the total composition; and
   d) a detergent additive in an amount effective for softening the composition, the detergent being selected from the group consisting sodium lauryl sulfate in an amount from about 1 to about 5 percent by weight based on the total weight of the composition of a sodium salt of fatty acid taurate in an amount from about 1 to about 5 percent by weight based on the total weight of the composition, an acyl glutamate in an amount from about one to about 19 weight percent based on the total weight of the composition, an α-olefin sulfonate in an amount from about one to about 15 weight percent based on the total weight of the composition, and a neutralized lauryl phosphoric acid in an amount from about 3 to about 7 weight percent based on the total weight of the composition.

2. A composition as in claim 1 further comprising microcrystalline wax.

3. A composition as in claim 2 wherein said microcrystalline wax is present in an amount from about 4 to 10% by weight based on the total weight of the composition.

4. A composition as in claim 1 wherein said emollients are selected from the group consisting of petrolalum, mineral oils, 1 Decene polymer (hydrogenated) and esters.

5. A composition as in claim 4 wherein said emollient is an ester selected from the group consisting of isopropyl palmitate, isopropyl myristate and $C_{12}$–$C_{15}$ alcohol benzoates.

6. A composition as in claim 1 further comprising a foam booster.

7. A composition as in claim 6 wherein said foam booster is selected from the group consisting of potassium polymetaphosphate, n-pentane, isopentane, sodium lauryl sulfate, sodium lauryl sulfoacetate, amides and sarcosynates.

8. A composition as in claim 6 wherein said foam booster is present in an amount up to about 5% by weight based on the weight of the total composition.

9. A composition as in claim 1 further comprising an active ingredient selected from the group consisting of deodorants, medicaments and antibacterial agents.

10. A composition as in claim 1 further comprising an active ingredient selected from the group consisting of coal tar, benzoyl peroxide, vitamin A, vitamin E, triclosan, PVP-Iodine and salicylic acid.

11. A composition as in claim 1 wherein the ratio of said detergent additive to sodium cocoyl isethionate is in the range of about 1:6 to about 1:1.

12. A composition as in claim 1 wherein said detergent additive is sodium lauryl sulfate and is present in an amount of about 1 to about 5 percent by weight of the total composition.

13. A composition as in claim 12 wherein sodium lauryl sulfate is present in an amount of about 3 percent by weight of the total composition.

14. A composition as in claim 12 wherein the ratio of sodium lauryl sulfate to sodium cocoyl isethionate is in the range of about 1:3 to about 1:6.

15. A composition as in claim 1 wherein sodium cocoyl isethionate is present in an amount from about 10 to about 19 percent by weight based on the weight of the total composition.

16. A composition as in claim 1 wherein acyl glutamate is the only detergent additive present in the composition.

* * * * *